United States Patent [19]

Meisel

[11] Patent Number: 4,867,683
[45] Date of Patent: Sep. 19, 1989

[54] ANCHORING DEVICE FOR DENTAL PROSTHESIS

[76] Inventor: Nicolas M. Meisel, Ferme du Mesnil, F78680, Epone, France

[21] Appl. No.: 865,738
[22] PCT Filed: Jun. 14, 1985
[86] PCT No.: PCT/FR85/00150
 § 371 Date: Apr. 16, 1986
 § 102(e) Date: Apr. 16, 1986
[87] PCT Pub. No.: WO86/00518
 PCT Pub. Date: Jan. 30, 1986

[30] Foreign Application Priority Data

Jul. 6, 1984 [FR] France .................. 84 10732

[51] Int. Cl.$^4$ .......................................... A61C 13/225
[52] U.S. Cl. .................................. 433/181; 433/180; 433/225
[58] Field of Search ............... 433/180, 181, 182, 183, 433/174, 220, 221, 225

[56] References Cited

U.S. PATENT DOCUMENTS

| | | | |
|---|---|---|---|
| 602,582 | 4/1898 | How | 433/221 |
| 1,199,109 | 9/1916 | Philbrook | 433/182 |
| 1,232,698 | 7/1917 | Lifshitz | 433/181 |
| 2,227,735 | 1/1941 | Morton | 433/219 |
| 2,536,669 | 1/1951 | Thau-Jensen | 433/221 |
| 2,672,686 | 3/1954 | Herzberg | 433/172 |
| 2,826,814 | 3/1958 | Sappey et al. | 433/193 |
| 3,717,931 | 2/1973 | Konig | 433/177 |
| 3,874,081 | 4/1975 | Franklin et al. | 433/225 |
| 4,163,318 | 8/1979 | Tigani | 433/172 |
| 4,172,323 | 10/1979 | Orlowski | 433/180 |
| 4,360,342 | 11/1982 | Salvo | 433/172 |
| 4,431,415 | 2/1984 | Tigani | 433/172 |
| 4,431,417 | 2/1984 | Weissman | 433/182 |

FOREIGN PATENT DOCUMENTS

| | | |
|---|---|---|
| 0022058 | of 0000 | European Pat. Off. . |
| 0025419 | of 0000 | European Pat. Off. . |
| 0037864 | of 0000 | European Pat. Off. . |
| 0061651 | of 0000 | European Pat. Off. . |
| 178689 | of 0000 | Fed. Rep. of Germany . |
| 71494 | of 0000 | France . |
| 1159575 | of 0000 | France . |
| 2188439 | of 0000 | France . |
| 2188440 | of 0000 | France . |
| 2274269 | of 0000 | France . |
| 2315901 | of 0000 | France . |
| 2387640 | of 0000 | France . |
| 2395738 | of 0000 | France . |
| 2464698 | of 0000 | France . |
| 2523838 | of 0000 | France . |

Primary Examiner—Gene Mancene
Assistant Examiner—Adriene J. Lepiane
Attorney, Agent, or Firm—Willian, Brinks, Olds, Hofer, Gilson & Lione

[57] ABSTRACT

An anchoring device for dental prosthesis applicable to both the reconstruction of deteriorated teeth and as a support for artificial teeth. The anchoring device includes a T-shaped anchoring element having a flattened head or bracket pierced with a hole, and a cylindrical leg provided with parallel grooves. The anchoring element is fixed in a healthy tooth after preparation and drilling. The anchoring element forms an armature or framework for reconstructed tooth material, or provides support for a U-shaped beam made of austenitic steel wire cloth. The U-shaped beam receives artificial teeth thereon to bridge an interdental space. The U-shaped beam is prevented from pivoting by vertically staggering the T-shaped elements.

3 Claims, 2 Drawing Sheets

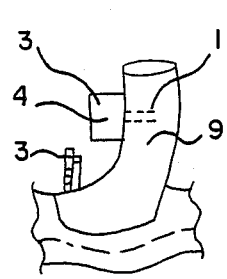
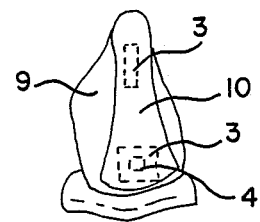
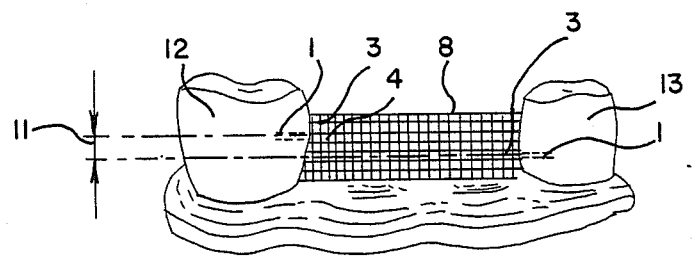
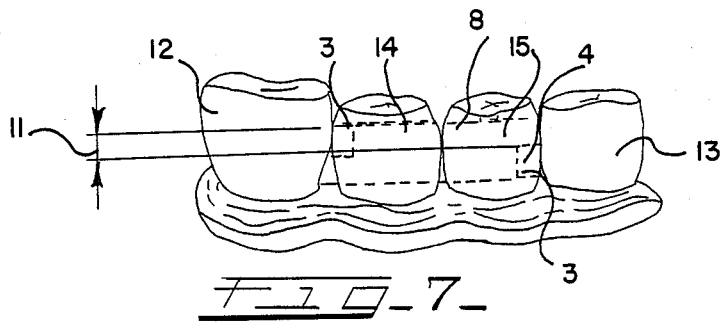

ANCHORING DEVICE FOR DENTAL PROSTHESIS

FIELD OF THE INVENTION

This invention relates to an anchoring device for dental prosthesis.

BACKGROUND OF THE INVENTION

The development of dental prostheses has focused on both longevity of operation of the prostehtic device as well as effectively anchoring the prosthetic device while causing the least possible harm to existing healthy teeth. Various unsuccessful attempts have been made to fulfill these requirements. In fact, the previously used prosthetics are either too flimsy or too sturdy for proper application, and may be difficult or even impossible to accurately adjust during usage.

SUMMARY OF THE INVENTION

The anchoring device of the present invention remedies these disadvantages by requiring that only a small hole be drilled in healthy teeth for the anchoring elements. Moreover, the anchoring elements withstand corrosion better, in addition to providing a larger fastening surface area than other prosthetics. This anchoring element can be used as an armature or foundation for the rebuilding of damaged teeth. It can also be used to anchor a beam across an interdental space to receive artificial teeth to replace missing teeth.

Essentially, the anchoring device of the present invention is comprised of a generally T-shaped anchoring element having a wide flattened bracket or head, containing a hole in the bracket. The T-shaped anchoring element is also provided with a cylindrical leg having several parallel axially concentric grooves.

The anchoring element is formed from a biosuitable metal having high structural qualities, such as titanium. The anchoring element is also sandblasted. The hole, grooves and sand-blasting of the anchoring element are intended to increase its bonding efficiency, both by increasing the bonding surface area and enhancing adhesion quality.

The anchoring device is further comprised of a beam formed by a U-shaped section with close set edges. The U-shaped section is made of a cloth or mesh of austenitic steel wire, for example.

In order to rebuild a damaged tooth, one or more T-shaped anchoring elements may be implanted in the healthy tooth near the section where a piece is missing. These elements act as an armature or framework for cavity-filling resinous material. These anchoring elements also offer a maximal adhesion surface area for the replacement tooth.

In replacing missing teeth with artificial teeth, one of the foregoing T-shaped anchoring elements is fixed to each of the side faces of the teeth defining an interdental space, and a beam made of the U-shaped metal cloth is adjusted for fit within the space. The U-shaped section is then jammed over the brackets of the T-shaped anchoring elements. The brackets are oriented with their major axes vertical, to this end. The T-shaped anchoring elements are staggered with respect to the height of the teeth into which they are placed. This prevents the risk of the angular displacement of the T-shaped anchoring element.

A non-limiting example of an embodiment of the present invention is described in the following detailed description in connection with the accompanying drawings, in which:

BRIEF DESCRIPTION OF THE DRAWINGS

FIG. 3 is an elevational view of T-shaped anchoring elements of the present invention fixed in the healthy portion of a damaged tooth;

FIG. 4 shows the tooth of FIG. 3 when repaired;

FIG. 5 is a left side view of FIG. 4;

FIG. 6 is an elevational view of the combined T-shaped elements and U-shaped metal cloth on which artificial teeth will be placed in an interdental space; and FIG. 7 is a view similar to FIG. 6 with artificial teeth in place.

DETAILED DESCRIPTION OF A PREFERRED EMBODIMENT

Figure 1:
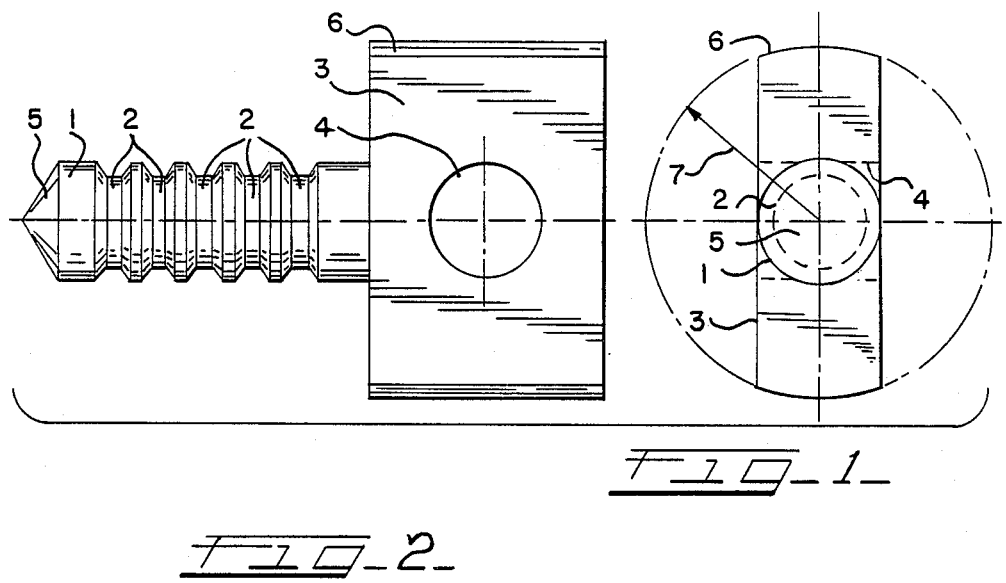
FIG. 1 is an elevational side view of a T-shaped anchoring element of the present invention, and end view of the T-shaped anchoring element.

As seen in FIG. 1, the T-shaped anchoring element of the present invention consists of a leg formed by a cylindrical stem 1 into which several grooves 2 are machined. The grooves 2 are concentric with the axis of the cylindrical stem 1. The cylindrical stem 1 has a generally constant radius, with a concial end 5. The T-shaped element further comprises a flattened bracket 3 which is pierced with a hole 4 in its center. The edges 6 of the bracket 3 are curved along the radius 7, as seen in the plan view of FIG. 1. A major axis for the bracket is defined between the edges 6.

Figure 2:
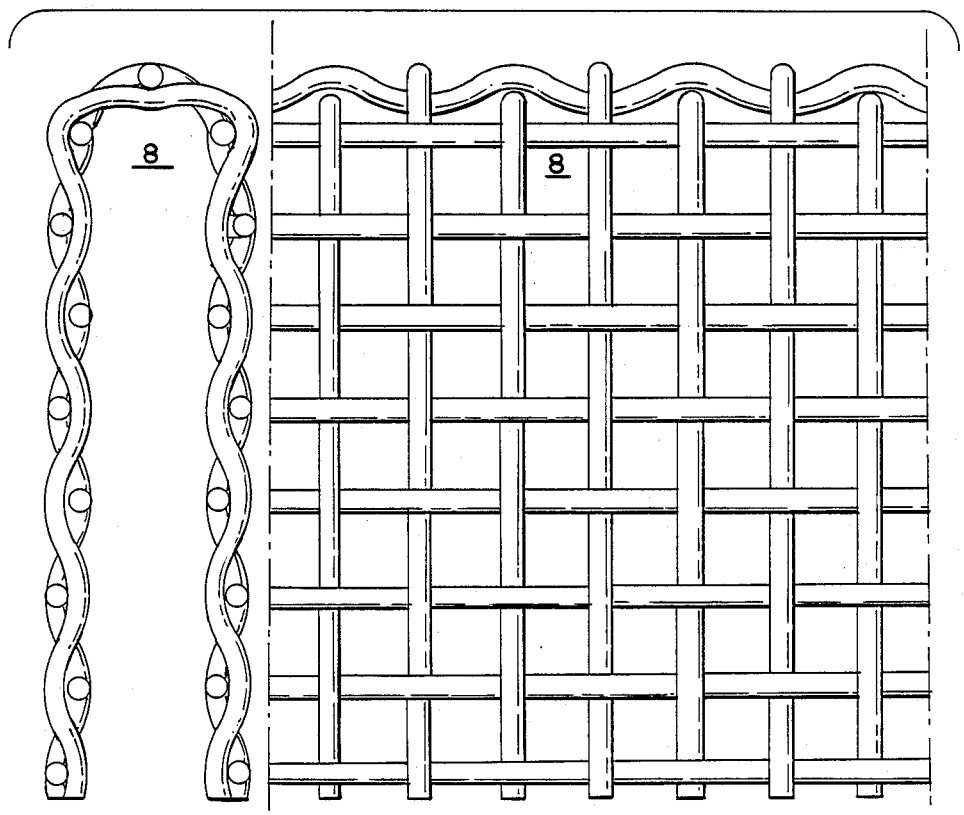
FIG. 2 is an end elevational view of a metal cloth U-section which forms the beam for carrying artificial teeth in an interdental space, and a partial side elevational view of the same.

A U-shaped beam 8, as seen in FIG. 2, is formed, for instance, from a metallic cloth or mesh section, such as austenitic steel wire. This U-shaped beam 8 is sized to engage and wrap around the flattened bracket 3 of the T-shaped anchoring element, as by jamming the beam thereon. This is done by applying a predetermined tightening stress on the U-shaped beam 8. The length of the U-shaped beam 8 is adjusted according to the size of the interdental space.

The rebuilding of a damaged tooth 9, as seen in FIGS. 3, 4 and 5, is accomplished, after conventional preparation of the tooth 9, by fixing a T-shaped anchoring element in the healthy part of the tooth 9. The tooth 9 is then rebuilt by filling the cavity with a molded resinous material 10 according to known methods.

As seen in FIG. 6, in order to replace a missing tooth or missing teeth, the T-shaped anchoring element is fixed on the sides of healthy teeth 12, 13 which form an interdental space. A vertical stagger (indicated at 11) is created between the height of placement of the T-shaped anchoring element in the teeth 12, 13 to prevent angular displacement, i.e. twisting.

The U-shaped beam 8 is then engaged astride the brackets 3 of each of the T-shaped anchoring elements after having been adjusted to the length of the interdental space. The anchoring elements are positioned with the major axis of the brackets extending generally parallel to the longitudinal axis of the adjacent teeth, i.e. the flattened sides extend up and down. The entire assembly is then coated with a compound material and then polymerized. In this way, an armature assembly for support of artificial teeth is created. Afterwards, the new teeth 14, 15 are molded in place on the armature assembly, buffed and polymerized for use.

It should be noted that the T-shaped anchoring element of the present invention is applicable to all forms of dental prosthetic operations. It is intended that the foregoing description be regarded as illustrative rather than limiting and that it be understood that it is the following claims, including all equivalents, which are intended to define the scope of this invention.

What is claimed is:

1. An anchoring device for a dental prosthesis comprising:
    a pair of anchoring elements, each of said anchoring elements having a cylindrical stem with a conical end and containing a plurality of parallel circular grooves, and a bracket formed as a head to said stem having a wide flat surface on opposite sides thereof through which a centrally located hole is formed, each of said stems configured for fixation in the side of a respective tooth of a pair of teeth defining an interdental space, such that each said bracket extends within the interdental space; and
    a U-shaped mesh, said mesh configured for placement over said brackets in a close fit with said brackets, said U-shaped mesh being permanently fixed in place on said brackets and being adapted to receive and form the sole support for prosthetic teeth thereafter fixed thereon to bridge the interdental space.

2. An anchoring device for a dental prosthesis comprising:
    a pair of anchoring elements, each of said anchoring elements having a cylindrical stem with a conical end and containing a plurality of parallel circular grooves, and a bracket formed as a head to said stem having a wide flat surface on opposite sides thereof through which a centrally located hole is formed, the flat surfaces of said bracket extending generally parallel to a plane defined by a tooth's longitudinal axis, each of said stems configured for fixation in the side of a respective tooth of a pair of teeth defining an interdental space, such that each said bracket is emplaced within the interdental space; and
    a U-shaped mesh, said mesh configured for placement over said brackets in a close fit with said brackets, said U-shaped mesh being adapted to receive prosthetic teeth thereon to bridge the interdental space, said anchoring elements being positioned with the brackets located at different vertical heights above the base of said interdental space thereby forming a stagger, said stagger created for the prevention of angular displacement of said mesh.

3. The anchoring device of claim 2, wherein said mesh is an austenitic steel wire mesh.

* * * * *